United States Patent [19]

Santana-Blank

[11] Patent Number: 5,231,984
[45] Date of Patent: Aug. 3, 1993

[54] LASER THERAPEUTIC APPARATUS

[75] Inventor: Luis A. Santana-Blank, Miami, Fla.

[73] Assignee: Lasb Laser, Corp., Miami, Fla.

[21] Appl. No.: 675,918

[22] PCT Filed: Dec. 11, 1989

[86] PCT No.: PCT/US89/05513
§ 371 Date: Apr. 26, 1991
§ 102(e) Date: Apr. 26, 1991

[51] Int. Cl.[5] .............................. A61N 5/06
[52] U.S. Cl. ..................... 128/395; 606/13; 606/2
[58] Field of Search .............. 128/395–398; 606/2–19

[56] References Cited

U.S. PATENT DOCUMENTS 4,765,322  8/1988  Charmillot et al. ........... 128/395
4,930,504  6/1990  Diamantopoulos et al. ..... 128/395

FOREIGN PATENT DOCUMENTS 2571264  4/1986  France ........................ 128/395

Primary Examiner—David M. Shay
Attorney, Agent, or Firm—J. Sanchelima

[57] ABSTRACT

An apparatus and method (10) for treating cancerous tissues and other systemic diseases through the application of an infrared laser beam to the target tissue through the biological circuit of the patient. The output of an oscillator (20) is connected to the input of a frequency selector (30) to selectively adjust the pulse frequency. The pulse train (40) is selected to be between 0.5 MHz and 7.5 MHz with a relatively low duty cycle to avoid thermic energy from making the process an uncomfortable one. The pulse signal, after being amplified, is fed to a transistor (50) that drives a laser diode (60) thereby modulating the output beam. An ultraviolet filter (70) is used to block any unwanted harmonic byproduct. The laser beam is applied substantially perpendicularly to the surface of the patient's skin and in the area in close proximity to the VICC biological circuit that would more efficiently carry the laser energy to the target tissue. The procedure is repeated periodically and its process monitored through conventional magnetic resonance images techniques or other accepted methods.

3 Claims, 1 Drawing Sheet

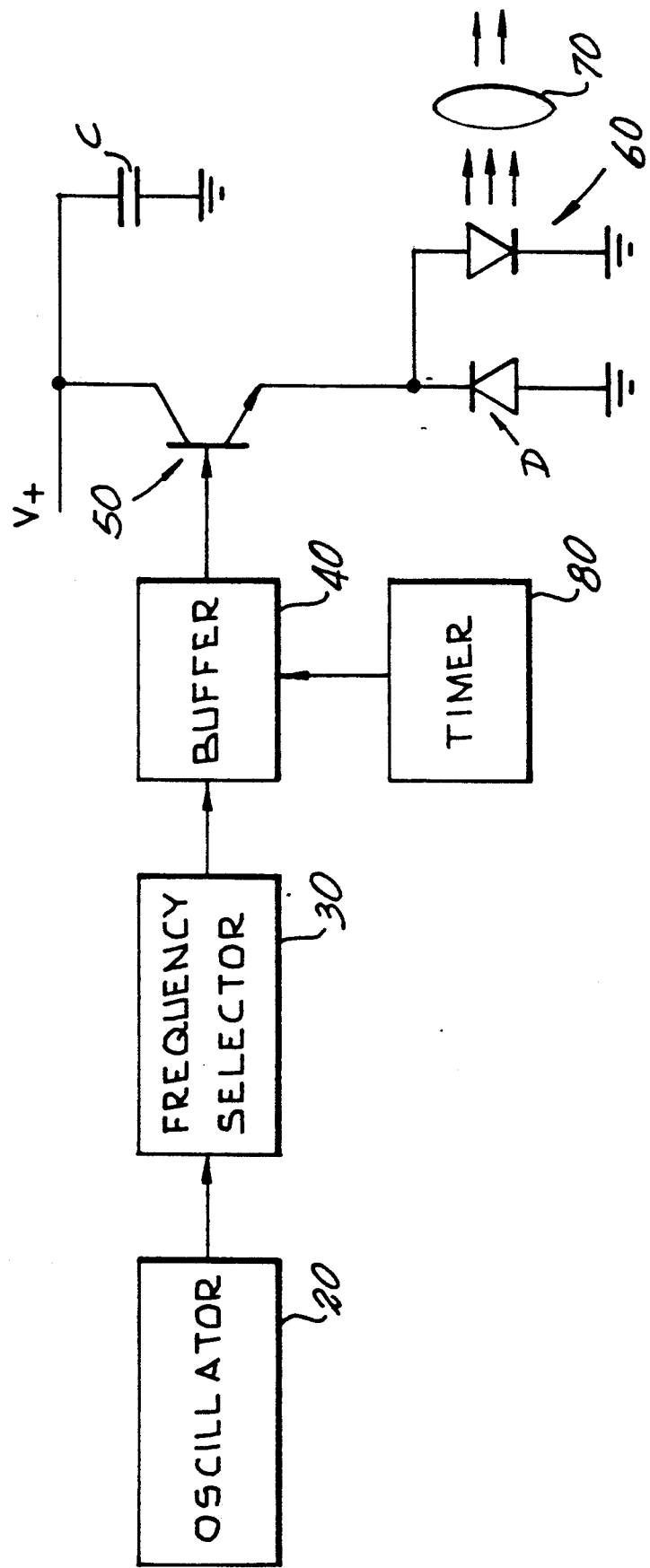

LASER THERAPEUTIC APPARATUS

TECHNICAL FIELD

The present invention relates to laser devices, and more particularly, to such devices that are used to treat cancer and other systemic diseases.

BACKGROUND ART

Applicant believes that the closest reference corresponds to U.S. Pat. No. 4,724,835 issued to Liss et al on Feb. 16, 1988. However, it differs from the present invention because this patented device includes a circuit that operates the infrared laser diode at a relatively high voltage with low pulse frequency. Also, while acknowledging or suggesting that the rise and/or fall time of the pulse may have an effect on the therapeutic effect of the above reference patented device, it nevertheless lacks any mechanism (electronic or otherwise) to optimize this parameter. In fact, the patentees acknowledge their lack of precise knowledge for the results obtained. Finally, in Liss' patent, the laser beam is applied specifically on the injury area with the consequent inadequacy for uniform treatment of systemic illnesses at a distance.

Other patents describing therapeutic devices that utilize the laser technology concentrate on the cutting and burning characteristics of these beams at their different wavelengths which are not the subject of the present invention. None of these patents suggest the novel features of the present invention.

Another related reference is the article written by Dr. Bjorn E. W. Northerstrom entitled "Biokinetic Impacts on Structure and Imaging of the Lung: The Concept of Biologically Closed Electric Circuits" and published in the September, 1985 issue of the American Journal of the Roentgen Ray Society. In this article, the concept of the Vascular-Interstitial Closed Circuit (VICC) is described. The VICC concept explains the different voltage potential drops observed by Dr. Northerstrom in the different tissues studied with direct electric current. This circuit comprises the entire circulatory system and through which the relatively low electric resistance of the plasma allows the flow of the direct current.

Another relevant reference in the related art includes the chapter authored by Dr. Anthony S-Y Leong entitled Microwave Irradiation in Histopathology in the volume 23, of part 2, of the Pathology Annual published Appleton & Lange, Norwalk, Conn. In particular, on the last paragraph of page 214 the author acknowledges the effect of field-induced alterations in macromolecular hydrogen bonding, proton tunnelling and disruption of bound water may induce alterations in biologic systems. This article, however, relates only to microwave fields.

For studies relating to lower frequency (ultra-sound on fractures) treatments, the closest reference known by Applicant corresponds to the article authored by A. A. Pilla et al in the Proceedings of the Annual International Conference of the IEEE Engineering in Medicine and Biology Society. (IEEE Cat. No. 88CH2566-8), New Orleans, La. 1988.

SUMMARY OF THE INVENTION

It is one of the main objects of the present invention to provide a laser apparatus and method for treating cancer and other systemic diseases through the alteration of the bonding of the water molecules which represent approximately 70% of all tissue structures and the transfer of the laser energy to the different biochemical structures and stimulation of their respective electrochemical pumps.

It is another object of this invention to provide a laser apparatus and method for treating cancer and other systemic diseases that can be readily and uniformly applied systemically by directing the laser energy to the subject tissue at a distance through the patient's vascular-interstitial closed electric circuit (VICC).

It is yet another object of the present invention to provide such a device that is relatively inexpensive to manufacture and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which:

FIG. 1 represents a block diagram of the apparatus for generating a pulsed laser beam to be used in the present invention.

DETAILED DESCRIPTION OF THE PREFERRED EMBODIMENT

Referring now to FIG. 1, where the present invention is generally referred to with numeral 10, it can be observed that it basically includes oscillator circuit 20 which in the preferred embodiment generates a signal to frequency selector circuit 30 which includes an electronic divider that can be readily adjusted thereby reducing and shaping the signal from oscillator 20. It has been found that best results are obtained when the frequency of the signal is between 0.5 MHz and 7.5 MHz. This signal is shaped in the form of square pulses, preferably, and amplified through buffer circuit 40 to activate transistor 50. The time of application is controlled with timer circuit 80. Transistor 50 is implemented in the preferred embodiment a bipolar transistor. Transistor 50 is switched on and off with the pulses received from buffer circuit 40 driving lasing diode 60. Lasing diode 60 is preferably implemented with a single heterojunction stacked diode, such as the one manufactured by Laser Diode, Inc. (Brunswick, N.J.) under part number LD-160, which has a peak wavelength of emission at 904 nanometers. The resulting laser beam is then passed through an ultraviolet filter 70 that blocks out higher harmonics, including potentially harmful ultraviolet components. It is important to note from the manufacturer specifications that laser diodes are typically driven at 1 KHz pulse frequencies and that they become considerably inefficient as the frequency is increased. At 0.5 MHz the efficiency is very low and this is not a range of operation recommended by the manufacturer. This inventor, however, is not interested in efficiency of the component but rather in radiating infrared laser energy that when modulated with relatively high frequency pulses (0.5 MHz to 7.5 MHz equivalent to those in the ultrasonic range) stimulates the natural physiological cell function. At these relatively high pulsated frequencies the radiated power is kept to a minimum in order to avoid discomfort to the patient.

In practice, the method for using the apparatus described above involves the positioning of the laser beam substantially perpendicularly over the patient's skin in the closest proximity of the most direct and efficient biological circuit in accordance with the concepts of VICC described in the above referenced article of Dr. Northerstrom which is hereby incorporated by reference.

It is well known that approximately 70% of the body weight of human and animal tissues are composed of water. It is also well established that water is inherently a good receptor for infrared radiations, including the pristine laser infrared wavelengths. By channeling the pulsed infrared laser energy produced by the above referenced apparatus through the VICC circuit of the patient to target tissues, electronic macromolecular bonding of the water is altered along the path and at the tissues. The transfer of energy accomplished with the present method is substantially more effective than the transfer studied by Dr. Anthony S-Y Leong with the microwave radiations since the latter has a larger thermic (and destructive) component that cannot be effectively utilized to stimulate the natural repair mechanisms residing on each cell. Dr. Leong was primarily concerned with the rapid fixation of tissues for biopsy. The natural repair mechanisms include calcium pumps, hydrogen pumps, cATP (system for high energy vinculated to phosphate) etc., when stimulated by the laser energy transferred, increase their opposition to the anarchical dispositions of the molecular structures of cancerous cells or other cellular dysfunctions.

In practice, the inventor's initial basic investigation involved the evaluation of severe lesions induced by heat on the skin of rats. In the experiment, seven groups of rats were created. In groups one through six, each rat was applied a 150 degrees centigrade soldering tip for approximately 1 minute. In group 1, the rats were applied an infrared laser beam pulsed at 3.0 MHz on the lesion immediately after burning. Then a specimen of the skin was obtained and the rats sacrificed. In group 2, the laser beam was applied immediately upon the infliction of the burn and 24 hours afterwards. The skin specimen was then taken. In group 3, the laser beam was applied immediately after the burn, 24 hours after and then again 48 hours after the infliction of the lesion. Then the skin sample was taken. Groups 4 through 6 were similar to groups 1 through 3, except that the laser radiation was not applied. Finally, group 7 was the control group and nothing was done to the rats of this group. The skin samples were measured by pulsed nuclear magnetic resonance methods and the water structure was found to be progressively better (closer to healthy) structured in the groups that were most exposed to the laser radiation. The percent of error (the value of p) found in this experiment was less than 0.54%. This is clear evidence of the certainty of the experiment supporting the foregoing deduction.

After this animal experiment, a pilot experimental project was initiated in Venezuela with 16 terminal patients with at least 12 weeks of expected lifetime. The patients had different carcinoma and sarcomas. The patients were examined every 5-8 weeks using magnetic resonance imaging methods to monitor the progress of the treatment. Additionally, laboratory routines, tumor markers and occasionally radiological procedures were utilized. All patients received the abovementioned pulsed infrared laser radiation at 3.0 MHz through the most effective VICC circuit for their particular case. These patients received multiple daily doses for periods of not less than 4 months and some of them for up to 11 months. It was observed that the tumoral activity was progressively reduced by its periodic monitoring through the abovementioned MRI methods. More recently, through serialized biopsy of the tumoral areas. The latter confirmed the changes announced by the MRI results. These results unequivocally establish a correlation between the application of the above referenced laser energy to the target tissues and the stimulation of the natural healing mechanisms of the body with the consequent involution of the tumor.

It is believed the foregoing description conveys the best understanding of the objects and advantages of the present invention. Different embodiments may be made of the inventive concept of this invention. It is to be understood that all matter disclosed herein is to be interpreted merely as illustrative, and not in a limiting sense.

INDUSTRIAL APPLICABILITY

It is apparent from the previous paragraphs that an improvement of the type for such a laser apparatus and method is quite desirable for treating cancer and other systemic diseases through the alteration of the bonding of the water molecules which represent approximately 70% of all tissue structures and the transfer of the laser energy to the different biochemical structures and stimulation of their respective electrochemical pumps.

What is claimed is:

1. An apparatus for treating cancerous tissues and other systemic diseases in humans and animals of the type that includes an infra-red laser diode and an oscillator circuit for generating pulses that activate said diode generating an infra-red laser radiation that is applied through the user's VICC biological circuit and the improvement comprising means for generating said pulses with a frequency between 0.5 megahertz and 7.5 megahertz with a relatively low radiant power so that thermic radiation as a byproduct is kept to a minimum.

2. The apparatus set forth in claim 1 further including filter means for limiting the application to a user of non-infrared radiation.

3. The apparatus set forth in claim 2 further including programmable timing means for pre-setting times of application.

* * * * *